(12) United States Patent
Liu et al.

(10) Patent No.: US 10,758,894 B2
(45) Date of Patent: Sep. 1, 2020

(54) SAPO-34/ZSM-5@ KAOLIN MICROSPHERE COMPOSITE CATALYTIC MATERIAL AND ITS PREPARATION AND USE

(71) Applicant: China University of Petroleum-Beijing, Beijing (CN)

(72) Inventors: Haiyan Liu, Beijing (CN); Lina Zhang, Beijing (CN); Xiaojun Bao, Beijing (CN)

(73) Assignee: China University of Petroleum-Beijing, Beijing (CN)

( * ) Notice: Subject to any disclaimer, the term of this patent is extended or adjusted under 35 U.S.C. 154(b) by 32 days.

(21) Appl. No.: 16/237,857

(22) Filed: Jan. 2, 2019

(65) Prior Publication Data

US 2019/0224652 A1   Jul. 25, 2019

(30) Foreign Application Priority Data

Jan. 23, 2018   (CN) .......................... 2018 1 00631967

(51) Int. Cl.
*B01J 29/00*      (2006.01)
*B01J 29/85*      (2006.01)
(Continued)

(52) U.S. Cl.
CPC .............. *B01J 29/005* (2013.01); *B01J 21/04* (2013.01); *B01J 21/08* (2013.01); *B01J 21/12* (2013.01);
(Continued)

(58) Field of Classification Search
CPC . B01J 29/005; B01J 29/85; B01J 29/40; B01J 21/04; B01J 21/12; B01J 21/08;
(Continued)

(56) References Cited

U.S. PATENT DOCUMENTS 4,440,871 A    4/1984   Lok et al.

FOREIGN PATENT DOCUMENTS

CN    102294262 A    12/2011
CN    103663483 A     3/2014
(Continued)

OTHER PUBLICATIONS

Is Li et al. ("Synthesis of SAPO-34/ZSM-5 Composite and Its Catalytic Performance in the Conversion of Methanol to Hydrocarbons", J. Braz. Chem. Soc., vol. 26, No. 2, p. 290-296). (Year: 2015).*

(Continued)

*Primary Examiner* — Ali Z Fadhel
(74) *Attorney, Agent, or Firm* — Young Basile Hanlon & MacFarlane, P.C.

(57) ABSTRACT

The present invention relates to a composite catalytic material of SAPO-34/ZSM-5@kaolin microspheres and its preparation and use, the method comprises the steps of: 1) processing kaolin into kaolin microspheres, and baking them to obtain activated kaolin microspheres; 2) mixing the activated kaolin microspheres obtained in step 1), water, a phosphorus source, and a template agent to prepare a gel; 3) mixing the gel obtained in step 2) and a ZSM-5 molecular sieve, and carrying out aging, crystallization, and separation to obtain a composite material of SAPO-34/ZSM-5@kaolin; 4) subjecting the composite material obtained in step 3) to ammonium exchange treatment and baking, to obtain the composite catalytic material of SAPO-34/ZSM-5@kaolin microspheres. The present invention not only greatly shortens the preparation route for the catalyst and reduces the cost of catalyst preparation, but also allows adjustment of the fractions of SAPO-34 and ZSM-5 molecular sieves in the composite material by adjustment of the synthesis conditions.

20 Claims, 9 Drawing Sheets

(51) Int. Cl.
*B01J 29/40* (2006.01)
*B01J 21/04* (2006.01)
*B01J 21/12* (2006.01)
*B01J 21/08* (2006.01)
*B01J 37/00* (2006.01)
*B01J 37/30* (2006.01)
*B01J 35/08* (2006.01)
*B01J 35/02* (2006.01)
*B01J 37/02* (2006.01)
*B01J 37/06* (2006.01)
*B01J 37/04* (2006.01)
*B01J 37/08* (2006.01)
*B01J 37/03* (2006.01)
*C07C 1/24* (2006.01)
*B01J 21/16* (2006.01)

(52) U.S. Cl.
CPC .............. *B01J 21/16* (2013.01); *B01J 29/40* (2013.01); *B01J 29/85* (2013.01); *B01J 35/023* (2013.01); *B01J 35/08* (2013.01); *B01J 37/009* (2013.01); *B01J 37/0018* (2013.01); *B01J 37/0045* (2013.01); *B01J 37/0063* (2013.01); *B01J 37/0236* (2013.01); *B01J 37/035* (2013.01); *B01J 37/036* (2013.01); *B01J 37/04* (2013.01); *B01J 37/06* (2013.01); *B01J 37/08* (2013.01); *B01J 37/30* (2013.01); *C07C 1/24* (2013.01); *B01J 2229/186* (2013.01); *C07C 2521/04* (2013.01); *C07C 2521/08* (2013.01); *C07C 2529/40* (2013.01); *C07C 2529/70* (2013.01); *Y02P 20/52* (2015.11); *Y02P 30/42* (2015.11)

(58) Field of Classification Search
CPC ...... B01J 37/0018; B01J 37/009; B01J 37/30; B01J 35/08; B01J 37/0045; B01J 37/0063; B01J 35/023; B01J 37/0236; B01J 37/06; B01J 37/04; B01J 37/08; B01J 37/035; B01J 37/036; B01J 21/16; B01J 2229/186; B01J 2229/62; B01J 2229/64; B01J 35/002; B01J 35/02; B01J 2229/60; C07C 1/24; C07C 2529/70; C07C 2521/08; C07C 2521/04; C07C 2529/40; C07C 1/20; C07C 2529/85; Y02P 20/52; Y02P 30/42; C01B 33/40; C01B 39/026; C01B 39/54
See application file for complete search history.

(56) References Cited

FOREIGN PATENT DOCUMENTS

| | | |
|---|---|---|
| CN | 104971768 A | 10/2015 |
| CN | 105312082 A | 2/2016 |
| CN | 106582804 A | 4/2017 |

OTHER PUBLICATIONS

Chinese Office Action and Search Report for Application No. 201810063196.7 dated Sep. 2, 2019.

* cited by examiner

US 10,758,894 B2

SAPO-34/ZSM-5@ KAOLIN MICROSPHERE COMPOSITE CATALYTIC MATERIAL AND ITS PREPARATION AND USE

TECHNICAL FIELD

The present invention relate to the field of chemical industry, and in particular, to a composite catalytic material of SAPO-34/ZSM-5@kaolin microspheres, and its preparation and use.

BACKGROUND ART

With the growth of the global economy, the demand for lower olefins such as ethylene and propylene has been increasing. Current production of ethylene and propylene still heavily depend on petroleum. For instance, in China, 60% of ethylene is from steam cracking of naphtha, and propylene is mainly from by-products of steam cracking and catalytic cracking (FCC) of naphtha. Due to the over-exploitation of petroleum resources, the reservoir and supply of petroleum diminish over time, Therefore, the route for preparing lower olefins via methanol or dimethyl ether from coal or natural gas as the starting material, i.e. the methanol-to-olefin (MTO) process or the methanol-to-propylene (MTP) process, is the most promising alternative to the naphtha route for preparation of lower olefins such as ethylene and propylene. At present, the main active component of a catalyst for MTO is the aluminum phosphate molecular sieve SAPO-34, and the main active component of a catalyst for MTP is the ZSM-5 molecular sieve. The two molecular sieves have different acidity and pore structures, and thus are used in methanol conversion processes for production of ethylene and propylene, respectively.

SAPO-34 molecular sieve is a molecular sieve based on silicon, phosphorus and aluminum, developed by Union Carbide (US) (U.S. Pat. No. 4,440,871), has a Chabazite (CHA)-based channel structure having both 8- and 4-membered rings which interconnect to form a cage, and has an effective pore size of 0.43 to 0.50 nm. The ZSM-5 zeolite molecular sieve is a high-Si zeolite having a 2D straight channel structure developed in 1970s by Mobil (US). It has an MFI-type topological structure, belongs to the orthorhombic system, and is formed by connected $TO_4$ (T=Si, Al, Fe, etc.) tetrahedrons.

Although SAPO-34 and ZSM-5 show good catalytic performance in conversion of methanol into lower olefins, most catalysts for MTO or MTP currently used in industries are prepared by a "semi-synthetic" method in which a chemically synthesized molecular sieve is mixed with water, a matrix, a binder and the like and the mixture is stirred, beaten, dried and molded to obtain the catalysts. Catalysts prepared by such a "semi-synthetic" method have disadvantages such as non-uniform distribution of active components and blockage of channels by the binder.

SUMMARY OF INVENTION

An objective of the present invention is to provide a method for preparing a composite catalytic material of SAPO-34/ZSM-5@kaolin microspheres. The objective of the present invention is accomplished by using kaolin microspheres as the starting material to provide all the silicon and aluminum sources for synthesis of a SAPO-34 molecular sieve and as a matrix for growth of a molecular sieve, supplementing a phosphorus source, adding dry powder of the ZSM-5 molecular sieve during synthesis, and carrying out in situ crystallization.

Another objective of the present invention is to provide a composite catalytic material of SAPO-34/ZSM-5@kaolin microspheres.

Another objective of the present invention is to provide a method for producing an olefin from methanol.

In order to achieve the above objectives, in one aspect, the present invention provides a method for preparing a molecular sieve of SAPO-34/ZSM-5@kaolin microspheres, comprising the steps of:
1) processing kaolin into kaolin microspheres, and baking them to obtain activated kaolin microspheres;
2) mixing the activated kaolin microspheres obtained in step 1), water, a phosphorus source, and a template agent to prepare a gel;
3) mixing the gel obtained in step 2) and a ZSM-5 molecular sieve, and carrying out aging, crystallization, and separation to obtain a composite material of SAPO-34/ZSM-5@kaolin;
4) subjecting the composite material obtained in step 3) to ammonium exchange treatment and baking, to obtain the composite catalytic material of SAPO-34/ZSM-5@kaolin microspheres.

In the method according to the present invention, the silicon and aluminum sources in kaolin are used as starting materials for synthesis of a SAPO-34 molecular sieve, a phosphorus source is supplemented, and dry powder of a ZSM-5 molecular sieve is used as seeds, to synthesize the composite material of SAPO-34/ZSM-5@kaolin microspheres. By using the silicon and aluminum components in kaolin as a starting material for synthesis of a SAPO-34 molecular sieve according to the method, the cost of synthesis can be reduced, and the synthesized SAPO-34 molecular sieve and the ZSM-5 molecular sieve are uniformly distributed on the surface of the kaolin microspheres.

The silicon and aluminum sources provided by kaolin according to the present invention refer to the components of silicon and aluminum species for synthesis of molecular sieves, which are extracted from baked kaolin microspheres with hydrochloric acid or a NaOH solution and enter the reactant gel.

According to the method for preparation of the present invention, the kaolin microspheres in Step 1) may be prepared by a conventional method in the art; and according to some specific embodiments of the present invention, in Step 1) the kaolin microspheres are prepared by spray drying.

According to some specific embodiments of the present invention, in Step 1), kaolin microspheres are prepared by mixing kaolin with water and a binder, and then spray drying.

The binder may be a binder conventionally used in the art; and according to some specific embodiments of the present invention, in Step 1) the binder is selected from one or more of water glass, alumina sol, and silica sol.

According to some specific embodiments of the present invention, in Step 1), the mass ratio of kaolin to binder is 1.5 to 2.75.

According to some specific embodiments of the present invention, in Step 1), kaolin is pulverized and screened before being mixed with water and a binder.

According to some specific embodiments of the present invention, in Step 1), the baking temperature is 650° C. to 900° C., preferably 750° C. to 800° C.

According to some specific embodiments of the present invention, in Step 1), the baking duration is 1 to 6 h, preferably 3 to 4 h.

According to the method for preparation of the present invention, in Step 1), the kaolin microspheres may be prepared to a conventional size of kaolin microspheres in the art; and according to some specific embodiments of the present invention, in Step 1) the particle size of the kaolin microspheres is 80 to 100 μm.

According to some specific embodiments of the present invention, in Step 2), the molar ratio among the components is (4-6)R:(0.20-0.30)$SiO_2$:(0.58-1.85)$Al_2O_3$:(2.0-3.1)$P_2O_5$:(111-222)$H_2O$, wherein R is the template agent.

Therein the aluminum source and the silicon source are both from the kaolin microspheres.

According to some specific embodiments of the present invention, Step 2) comprises homogeneously mixing a phosphorus source with a part of water first, then adding a template agent and the rest of water, mixing them homogeneously, then adding the activated kaolin microspheres obtained in Step 1), and mixing them homogeneously to obtain a gel.

In Step 2), the activated kaolin microspheres, the template agent, the phosphorus source and water are added in the order of water, the phosphorus source, the template agent, water and the kaolin microspheres.

According to some specific embodiments of the present invention, in Step 2), the template agent is selected from one or more of triethylamine, diethylamine, and tetraethylammonium hydroxide.

According to some specific embodiments of the present invention, in Step 2), the phosphorus source is phosphoric acid.

According to some specific embodiments of the present invention, in Step 3), the mass ratio of ZSM-5 molecular sieve to gel is 0.042 to 0.066.

According to some specific embodiments of the present invention, in Step 3), the ZSM-5 molecular sieve is a ZSM-5 molecular sieve having not been subjected to template removal.

In Step 3) according to the present invention, the template agent for ZSM-5 is retained and can promote generation of ZSM-5 during in situ crystallization.

According to some specific embodiments of the present invention, in Step 3), the Si/Al molar ratio of the ZSM-5 molecular sieve is 50 to 200, preferably 50 to 150.

According to some specific embodiments of the present invention, in Step 3), the aging temperature is 40° C. to 90° C., preferably 70° C.

According to some specific embodiments of the present invention, in Step 3), the aging duration is 15 to 60 min, preferably 30 min.

According to some specific embodiments of the present invention, in Step 3), the crystallization temperature is 180° C. to 220° C.

According to some specific embodiments of the present invention, in Step 3), the crystallization temperature is 200° C.

According to some specific embodiments of the present invention, in Step 3), the crystallization duration is 24 to 72 h.

According to some specific embodiments of the present invention, in Step 3), the crystallization duration is 48 h.

According to some specific embodiments of the present invention, in Step 3), the crystallization is carried out at 180° C. to 220° C. for 24 to 72 h.

According to some specific embodiments of the present invention, in Step 3), the crystallization is carried out at 200° C. for 48 h.

According to some specific embodiments of the present invention, in Step 3), after the crystallization, steps of standing for precipitation, centrifuging, washing, and drying are carried out to obtain the composite material of SAPO-34/ZSM-5@kaolin.

According to some specific embodiments of the present invention, in Step 3), standing is carried out for 5 to 15 min for precipitation.

According to some specific embodiments of the present invention, in Step 3), the drying temperature is 100° C. to 120° C. and the drying duration is 4 to 12 h.

According to some specific embodiments of the present invention, Step 4) comprises subjecting the composite material obtained in step 3) to ammonium exchange treatment in an aqueous solution of ammonium chloride and then baking, to obtain the composite catalytic material of SAPO-34/ZSM-5@kaolin microspheres.

According to some specific embodiments of the present invention, in Step 4), the aqueous solution of ammonium chloride has a molar concentration of 0.1 to 1, preferably 0.8 M.

According to some specific embodiments of the present invention, Step 4) comprises stirring the composite material obtained in step 3) in an aqueous solution of ammonium chloride for 2 to 6 h at 60° C. to 90° C.

According to some specific embodiments of the present invention, Step 4) comprises stirring the composite material obtained in step 3) in an aqueous solution of ammonium chloride at 80° C.

According to some specific embodiments of the present invention, Step 4) comprises stirring the composite material obtained in step 3) in an aqueous solution of ammonium chloride for 4 h.

According to some specific embodiments of the present invention, Step 4) comprises stirring the composite material obtained in step 3) in an aqueous solution of ammonium chloride for 4 h at 80° C.

According to some specific embodiments of the present invention, in Step 4), the baking temperature is 500° C. to 600° C.

According to some specific embodiments of the present invention, in Step 4), the baking temperature is 550° C.

According to some specific embodiments of the present invention, in Step 4), the baking duration is 3 to 6 h.

According to some specific embodiments of the present invention, in Step 4), the baking duration is 4 h.

According to some specific embodiments of the present invention, in Step 4), the baking is carried out at 550° C. for 4 h.

Another aspect of the present invention provides a composite catalytic material of SAPO-34/ZSM-5@kaolin microspheres prepared by the method according to the present invention.

According to some specific embodiments of the present invention, based on the relative crystallinity, the relative content of the SAPO-34 molecular sieve is 7 to 15 wt %, and the relative content of the ZSM-5 molecular sieve is 6 to 12 wt %.

Yet another aspect of the present invention provides a method for producing olefins from methanol, in which an aqueous solution of methanol is used as a raw material and the composite catalytic material of SAPO-34/ZSM-5@kaolin microspheres according to the present invention is used as a catalyst.

According to some specific embodiments of the present invention, the aqueous solution of methanol has a concentration of 90 to 99 wt %, preferably 95 wt %.

According to some specific embodiments of the present invention, in the method, an aqueous solution of methanol is used as a raw material, the composite catalytic material of SAPO-34/ZSM-5@kaolin microspheres according to the present invention is used as a catalyst, and olefins are prepared at the conditions of normal pressure, a reaction temperature of 400 to 500° C., and a weight hourly space velocity (WHSV) of 2 to 3 h$^{-1}$.

According to some specific embodiments of the present invention, wherein the reaction temperature is 450° C.

According to some specific embodiments of the present invention, wherein the weight hourly space velocity (WHSV) is 2.5 h$^{-1}$ According to some specific embodiments of the present invention, in the method, an aqueous solution of methanol is used as a raw material, the composite catalytic material of SAPO-34/ZSM-5@kaolin microspheres according to the present invention is used as a catalyst, and olefins are prepared at the conditions of normal pressure, a reaction temperature of 450° C., and a weight hourly space velocity (WHSV) of 2.5 h$^{-1}$.

In summary, the present invention provides a molecular sieve of SAPO-34/ZSM-5@kaolin microspheres and its preparation and use. Embodiments of the present invention have the following advantages.

The present invention uses kaolin microspheres as both a matrix and a part of starting material to provide all the silicon source and aluminum source required for synthesis of a SAPO-34 molecular sieve, and introduces powder of a ZSM-5 molecular sieve during the synthesis as seeds to allow in situ growth of SAPO-34 and ZSM-5 on the kaolin microspheres and also allow uniform distribution of SAPO-34 and ZSM-5 molecular sieves on the surface of the kaolin microspheres, so as to prepare the composite material of SAPO-34/ZSM-5@kaolin microspheres. After subjecting ammonium exchange treatment and baking, the composite material can be directly used as an MTO catalyst and used in an MTO reactor, which not only greatly shortens the preparation route for the catalyst and reduces the cost of catalyst preparation, but also allows adjustment of the fractions of SAPO-34 and ZSM-5 molecular sieves in the composite material by adjustment of the synthesis conditions, and in turn allows adjustment of the acidity and channel structure of the composite material, avoids the drawback of blockage of channels in the molecular sieve by the matrix or a binder in a semi-synthetic method, and exerts a synergistic effect of the acidity and channel structure of SAPO-34 and ZSM-5 molecular sieves, thereby improving the selectivity for ethylene and propylene in an MTO reaction. In addition, due to the introduction of a ZSM-5 molecular sieve, the lifetime of the composite catalyst of SAPO-34/ZSM-5@kaolin microspheres in an MTO reaction is greatly prolonged.

DETAILED DESCRIPTION OF INVENTION

The implementation and beneficial effects of the present invention are described in detail below in combination with Examples to help readers better understand the spirit and features of the present invention, but the following description is not to limit the implementable scope of the present invention.

According to the present invention, the crystal phase structure of samples is determined by X-ray diffraction (XRD), and the morphology and form of crystal of samples were determined by field emission scanning electron microscopy (FESEM).

According to the present invention, the contents of SAPO-34 and ZSM-5 molecular sieves in the composite material are derived from the relative crystallinity. Relative crystallinity refers to the ratio of the area of characteristic peaks of each molecular sieve in an in situ crystallized product to that of a corresponding standard sample of the molecular sieve. The characteristic peaks of the SAPO-34 molecular sieve are peaks at 2θ of 9.5°, 16.0°, 20.5°, and 31°, and the characteristic peaks of the ZSM-5 molecular sieve are peaks at 2θ of 22.5 to 25°. The standard samples of the molecular sieves are the normal micro-porous SAPO-34 molecular sieve produced by Nankai University Catalyst Co. Ltd., and a self-made micro-porous ZSM-5 molecular sieve, the crystallinity of which are set as 100%.

Example 1

100 g kaolin, 350 g water, and 40 g alumina sol were homogeneously mixed and spray-dried to obtain kaolin microspheres, which were baked at 700° C. for 4 h and ready for use.

4 g phosphoric acid was weighed out and mixed with 10 g water. The mixture was stirred for 30 min, and 4 g triethylamine and 10 g water were added thereto under stirring, following by further stirring. 5 g kaolin microspheres were added, and the mixture was allowed to stand for 2 h. The resultant gel comprised the following components in a molar ratio of $4R:0.30SiO_2:1.85Al_2O_3:2P_2O_5:111H_2O$.

1.5 g dry powder of a ZSM-5 molecular sieve having a $SiO_2/Al_2O_3$ of 200, which had not been subjected to template removal, was weighed out and added to the above liquid mixture such that the mass ratio of ZSM-5 dry powder to gel was 0.045, followed by stirring at 40° C. for 30 min.

The resultant liquid mixture was transferred to a sealed high-pressure crystallizing kettle, and crystallization was carried out in a rotary oven at 180° C. for 24 h.

Figure 1:
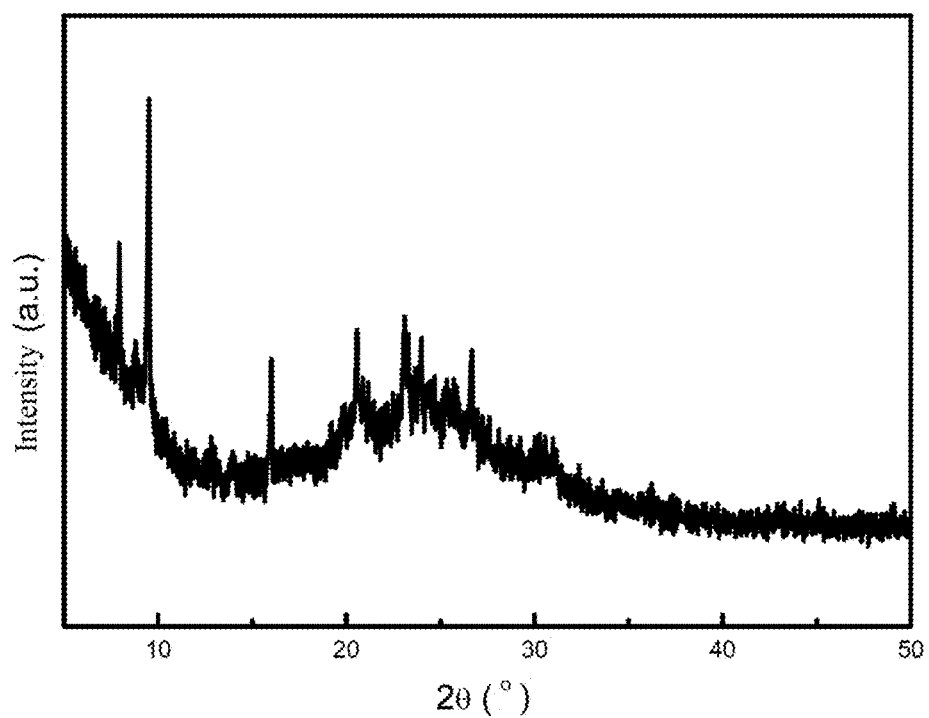
FIG. 1 is an X-ray diffraction (XRD) pattern of the composite material obtained in Example 1.
Figure 2A:
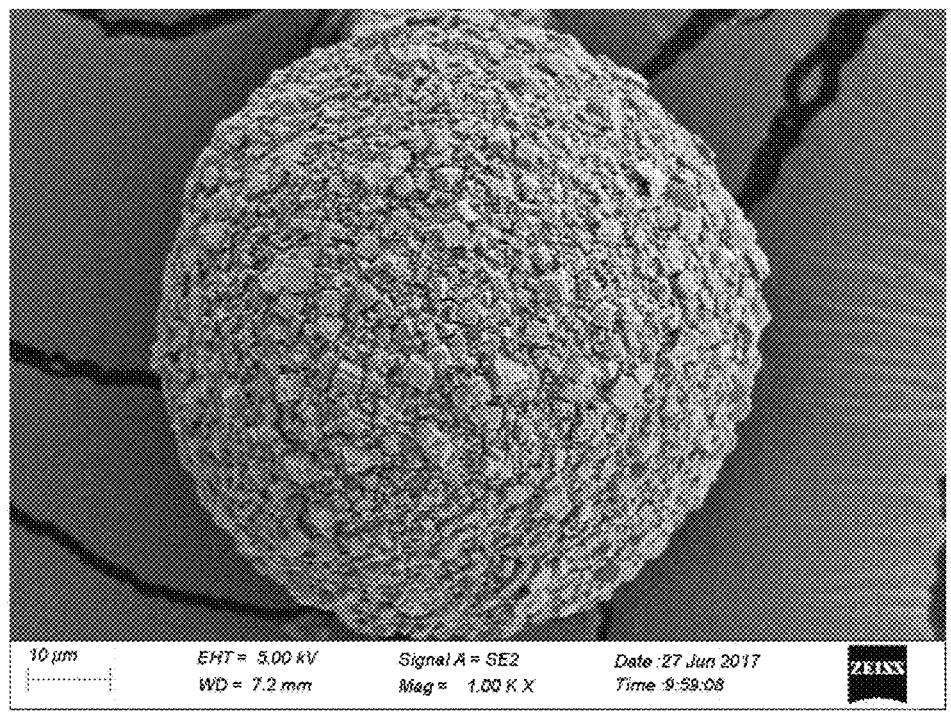
FIG. 2A is a 1000× magnification of a field emission scanning electron microscopy (FESEM) image of the composite material obtained in Example 1.
Figure 2B:
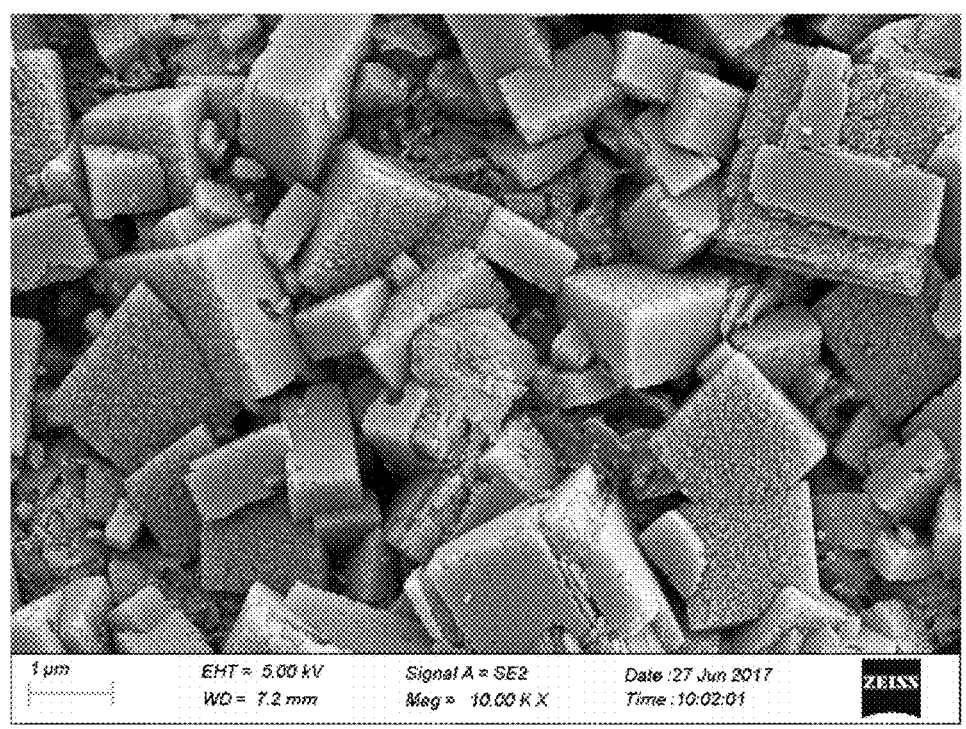
FIG. 2B is a 10000× magnification of a FESEM image of the composite material obtained in Example 1.

The product was taken out and allowed to stand and precipitate for 5 min. The non-in situ products in the upper layer of liquid were removed, and the precipitated in situ product was separated by centrifuging, washed, dried at 100° C. for 4 h, subjected to ammonium exchange treatment twice in 0.5 M ammonium chloride (in each exchange, the in situ product was put in an aqueous solution of ammonium chloride and stirred at 80° C. for 4 h), and baked at 520° C. for 3 h, to obtain a composite catalytic material of SAPO-34/ZSM-5@kaolin microspheres. After quantification by XRD, the content of SAPO-34 molecular sieve in the product was 7% by weight, and the content of ZSM-5 molecular sieve in the product was 9% by weight. The XRD pattern of the composite material is shown in FIG. 1, and the SEM images thereof are shown in FIG. 2.

Example 2

100 g kaolin, 350 g water, and 35 g alumina sol were homogeneously mixed and spray-dried to obtain kaolin microspheres, which were baked at 800° C. for 4 h and ready for use.

5 g phosphoric acid was weighed out and mixed with 15 g water. The mixture was stirred for 30 min, and 5 g triethylamine and 15 g water were added thereto under stirring, following by further stirring. 5 g kaolin microspheres were added, and the mixture was allowed to stand for 2 h. The resultant gel comprised the following components in a molar ratio of $5R:0.20SiO_2:1.47Al_2O_3:2.6P_2O_5:166H_2O$.

2 g dry powder of a ZSM-5 molecular sieve having a $SiO_2/Al_2O_3$ of 80, which had not been subjected to template removal, was weighed out and added to the above liquid mixture such that the mass ratio of ZSM-5 dry powder to gel was 0.044, followed by stirring at 70° C. for 30 min.

The resultant liquid mixture was transferred to a sealed high-pressure crystallizing kettle, and crystallization was carried out in a rotary oven at 200° C. for 48 h.

Figure 3:
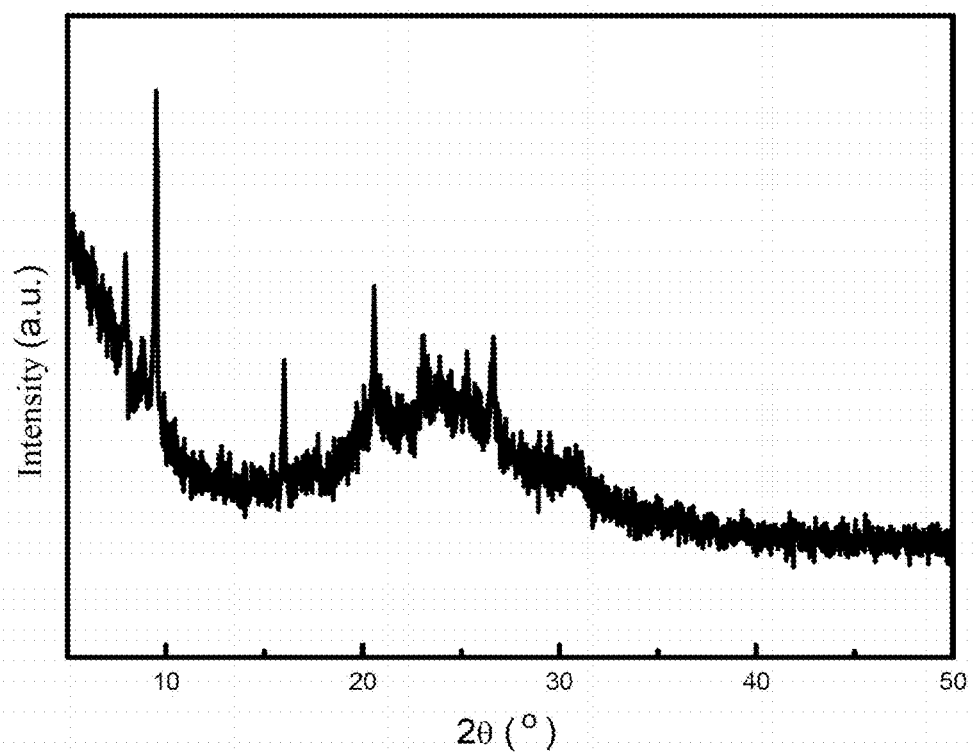
FIG. 3 is an XRD pattern of the composite material obtained in Example 2.

The product was taken out and allowed to stand and precipitate for 5 min. The non-in situ products in the upper layer of liquid were removed, and the precipitated in situ product was separated by centrifuging, washed, dried at 120° C. for 6 h, subjected to ammonium exchange treatment twice in 1.0 M ammonium chloride (in each exchange, the in situ product was put in an aqueous solution of ammonium chloride and stirred at 75° C. for 4 h), and baked at 550° C. for 4 h, to obtain a composite catalyst of SAPO-34/ZSM-5@kaolin microspheres. After quantification by XRD, the content of SAPO-34 molecular sieve in the product was 15% by weight, and the content of ZSM-5 molecular sieve in the product was 12% by weight. The XRD pattern of the composite material is shown in FIG. 3.

Example 3

100 g kaolin, 350 g water, 52 g alumina sol, and 15 g silica sol were homogeneously mixed and spray-dried to obtain kaolin microspheres, which were baked at 900° C. for 6 h and ready for use.

6 g phosphoric acid was weighed out and mixed with 20 g water. The mixture was stirred for 30 min, and 6 g triethylamine and 20 g water were added thereto under stirring, following by further stirring. 5 g kaolin microspheres were added, and the mixture was allowed to stand for 2 h. The resultant gel comprised the following components in a molar ratio of $6R:0.27SiO_2:0.58Al_2O_3:3.0P_2O_5:222H_2O$.

3.0 g dry powder of a ZSM-5 molecular sieve having a $SiO_2/Al_2O_3$ of 100, which had been subjected to template removal, was weighed out and added to the above liquid mixture such that the mass ratio of ZSM-5 dry powder to gel was 0.053, followed by stirring at 90° C. for 60 min.

The resultant liquid mixture was transferred to a sealed high-pressure crystallizing kettle, and crystallization was carried out in a rotary oven at 220° C. for 72 h.

Figure 4:
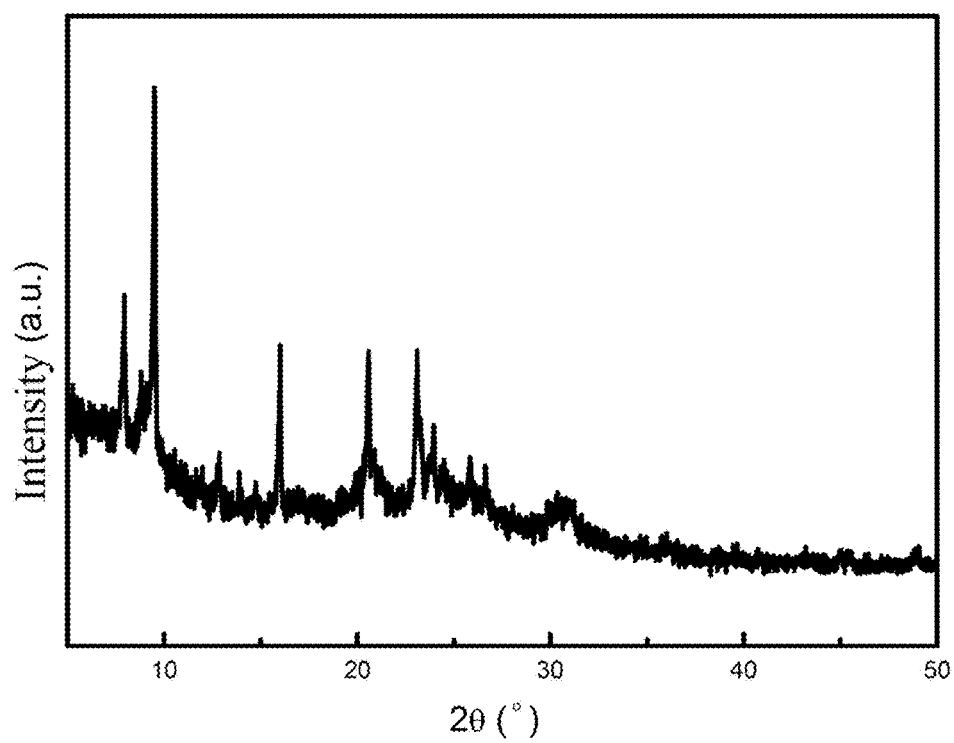
FIG. 4 is an XRD pattern of the composite material obtained in Example 3.

The product was taken out and allowed to stand and precipitate for 5 min. The non-in situ products in the upper layer of liquid were removed, and the precipitated in situ product was separated by centrifuging, washed, dried at 110° C. for 12 h, subjected to ammonium exchange treatment twice in 0.1 M ammonium chloride (in each exchange, the in situ product was put in an aqueous solution of ammonium chloride and stirred at 60° C. for 6 h), and baked at 600° C. for 6 h, to obtain a composite molecular sieve of SAPO-34/ZSM-5@kaolin microspheres. After quantification by XRD, the content of SAPO-34 molecular sieve in the product was 10% by weight, and the content of ZSM-5 molecular sieve in the product was 7.5% by weight. The XRD pattern of the composite material is shown in FIG. 4.

Example 4

100 g kaolin, 350 g water, and 45 g alumina sol were homogeneously mixed and spray-dried to obtain kaolin microspheres, which were baked at 800° C. for 4 h and ready for use.

5 g phosphoric acid was weighed out and mixed with 15 g water. The mixture was stirred for 30 min, and 5 g triethylamine and 15 g water were added thereto under stirring, following by further stirring. 5 g kaolin microspheres were added, and the mixture was allowed to stand for 2 h. The resultant gel comprised the following components in a molar ratio of $5R:0.20SiO_2:1.47Al_2O_3:2.6P_2O_5:166H_2O$.

2 g dry powder of a ZSM-5 molecular sieve having a $SiO_2/Al_2O_3$ of 50, which had not been subjected to template removal, was weighed out and added to the above liquid mixture such that the mass ratio of ZSM-5 dry powder to gel was 0.044, followed by stirring at 70° C. for 30 min.

The resultant liquid mixture was transferred to a sealed high-pressure crystallizing kettle, and crystallization was carried out in a rotary oven at 200° C. for 48 h.

Figure 5:
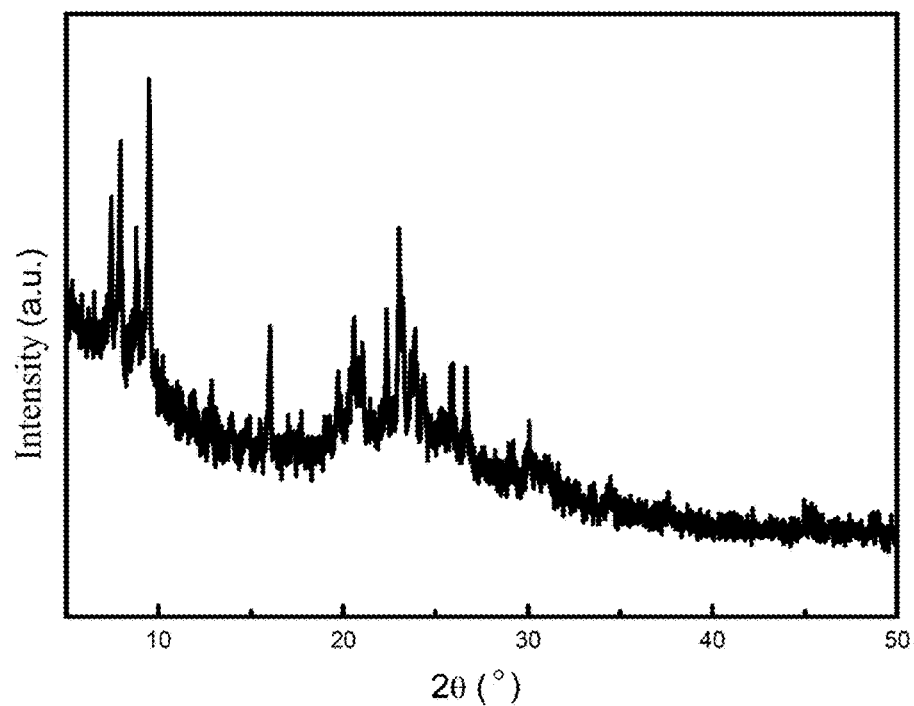
FIG. 5 is an XRD pattern of the composite material obtained in Example 4.

The product was taken out and allowed to stand and precipitate for 5 min. The non-in situ products in the upper layer of liquid were removed, and the precipitated in situ product was separated by centrifuging, washed, dried at 105° C. for 8 h, subjected to ammonium exchange treatment twice in 0.6 M ammonium chloride (in each exchange, the in situ product was put in an aqueous solution of ammonium chloride and stirred at 65° C. for 5 h), and baked at 550° C. for 4 h, to obtain a composite molecular sieve of SAPO-34/ZSM-5@kaolin microspheres. After quantification by XRD, the content of SAPO-34 molecular sieve in the product was 11% by weight, and the content of ZSM-5 molecular sieve in the product was 6% by weight. The XRD pattern of the composite material is shown in FIG. 5.

Example 5

100 g kaolin, 350 g water, and 40 g alumina sol were homogeneously mixed and spray-dried to obtain kaolin microspheres, which were baked at 800° C. for 4 h and ready for use.

5 g phosphoric acid was weighed out and mixed with 15 g water. The mixture was stirred for 30 min, and 7.35 g tetraethylammonium hydroxide and 15 g water were added thereto under stirring, following by further stirring. 5 g kaolin microspheres were added, and the mixture was allowed to stand for 2 h. The resultant gel comprised the following components in a molar ratio of $5R:0.20SiO_2:1.47Al_2O_3:2.6P_2O_5:166H_2O$.

2 g dry powder of a ZSM-5 molecular sieve having a $SiO_2/Al_2O_3$ of 50, which had been subjected to template removal, was weighed out and added to the above liquid mixture such that the mass ratio of ZSM-5 dry powder to gel was 0.042, followed by stirring at 70° C. for 30 min.

The resultant liquid mixture was transferred to a sealed high-pressure crystallizing kettle, and crystallization was carried out in a rotary oven at 200° C. for 48 h.

Figure 6:
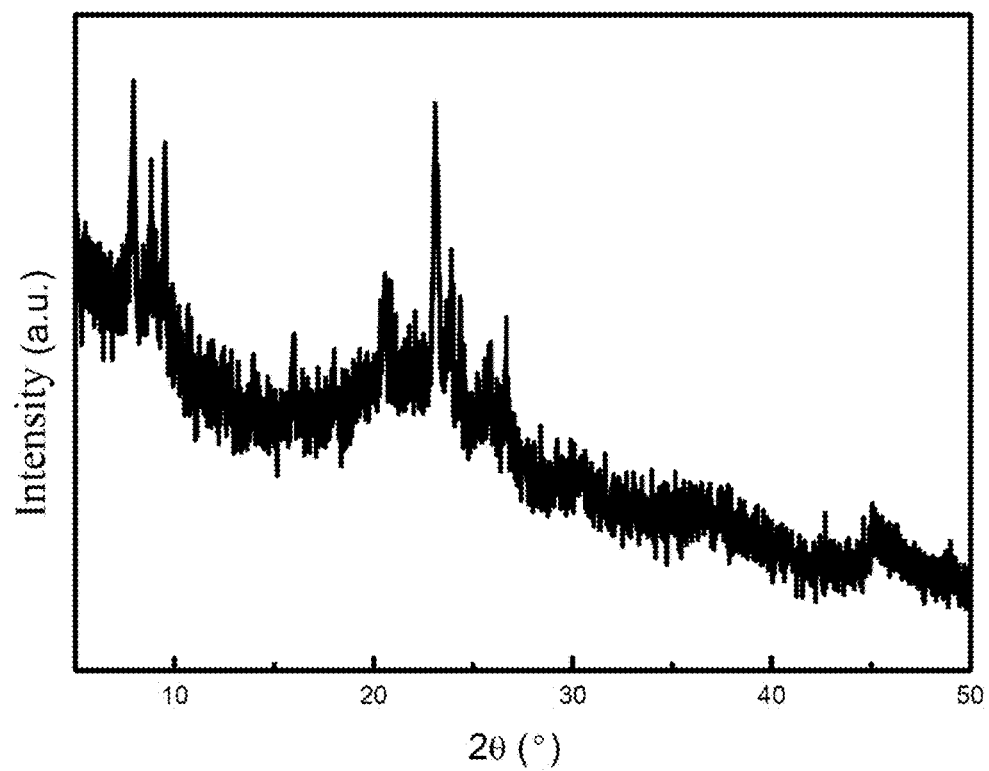
FIG. 6 is an XRD pattern of the composite material obtained in Example 5.

The product was taken out and allowed to stand and precipitate for 5 min. The non-in situ products in the upper layer of liquid were removed, and the precipitated in situ product was separated by centrifuging, washed, dried at 120° C. for 6 h, subjected to ammonium exchange treatment twice in 0.5 M ammonium chloride (in each exchange, the in situ product was put in an aqueous solution of ammonium chloride and stirred at 85° C. for 2 h), and baked at 550° C. for 4 h, to obtain a composite molecular sieve of SAPO-34/ZSM-5@kaolin microspheres. This product has an XRD pattern similar to that of the product prepared in Example 2. The content of SAPO-34 molecular sieve in the product was 10% by weight, and the content of ZSM-5 molecular sieve in the product was 7% by weight. The XRD pattern of the composite material is shown in FIG. 6.

Example 6

100 g kaolin, 350 g water, and 40 g alumina sol were homogeneously mixed and spray-dried to obtain kaolin microspheres, which were baked at 800° C. for 4 h and ready for use.

5 g phosphoric acid was weighed out and mixed with 15 g water. The mixture was stirred for 30 min, and 3.65 g diethylamine and 15 g water were added thereto under stirring, following by further stirring. 5 g kaolin microspheres were added, and the mixture was allowed to stand for 2 h. The resultant gel comprised the following components in a molar ratio of $5R:0.20SiO_2:1.47Al_2O_3:2.6P_2O_5:166H_2O$.

2 g dry powder of a ZSM-5 molecular sieve having a $SiO_2/Al_2O_3$ of 50, which had not been subjected to template removal, was weighed out and added to the above liquid mixture such that the mass ratio of ZSM-5 dry powder to gel was 0.046, followed by stirring at 70° C. for 30 min.

The resultant liquid mixture was transferred to a sealed high-pressure crystallizing kettle, and dynamic crystallization was carried out at 200° C. for 48 h.

Figure 7:
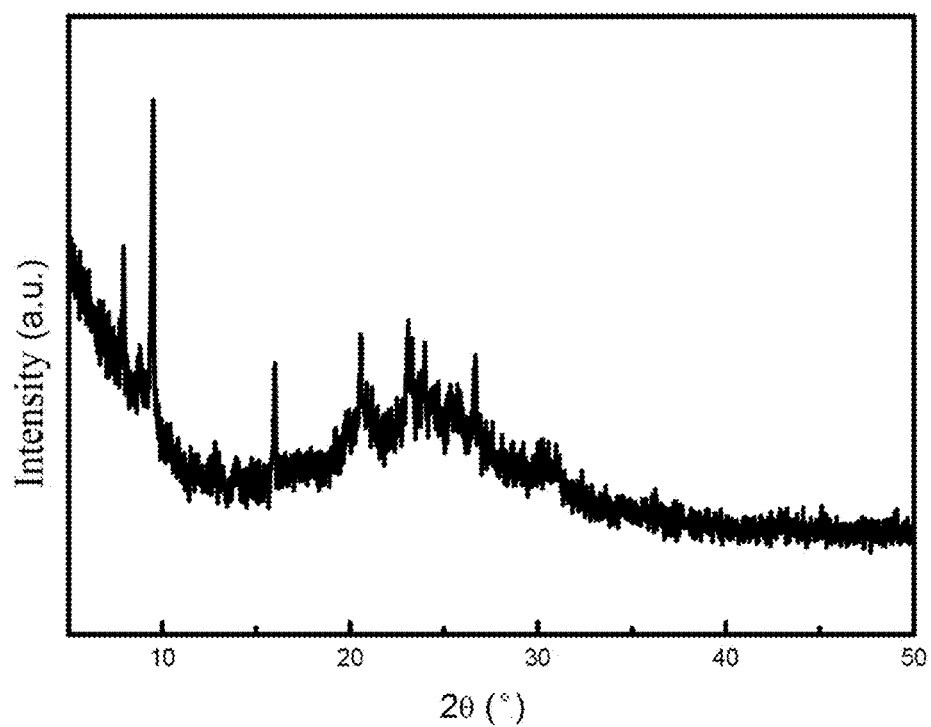
FIG. 7 is an XRD pattern of the composite material obtained in Example 6.

The product was taken out and allowed to stand and precipitate for 5 min. The non-in situ products in the upper layer of liquid were removed, and the precipitated in situ product was separated by centrifuging, washed, dried at 120° C. for 6 h, subjected to ammonium exchange treatment twice in 0.5 M ammonium chloride (in each exchange, the in situ product was put in an aqueous solution of ammonium chloride and stirred at 90° C. for 3 h), and baked at 550° C. for 4 h, to obtain a composite molecular sieve of SAPO-34/ZSM-5@kaolin microspheres. This product has an XRD pattern similar to that of the product prepared in Example 2. The content of SAPO-34 molecular sieve in the product was 11% by weight, and the content of ZSM-5 molecular sieve in the product was 6.5% by weight. The XRD pattern of the composite material is shown in FIG. 7.

Example 7

100 g kaolin, 350 g water, and 36 g silica sol were homogeneously mixed and spray-dried to obtain kaolin microspheres, which were baked at 800° C. for 4 h and ready for use.

5 g phosphoric acid was weighed out and mixed with 15 g water. The mixture was stirred for 30 min, and 1.33 g diethylamine, 3.67 g tetraethylammonium hydroxide and 15 g water were added thereto under stirring, following by further stirring. 5 g kaolin microspheres were added, and the mixture was allowed to stand for 2 h. The resultant gel comprised the following components in a molar ratio of $5R:0.20SiO_2:1.47Al_2O_3:2.6P_2O_5:166H_2O$.

2 g dry powder of a ZSM-5 molecular sieve having a $SiO_2/Al_2O_3$ of 60, which had not been subjected to template removal, was weighed out and added to the above liquid mixture such that the mass ratio of ZSM-5 dry powder to gel was 0.044, followed by stirring at 70° C. for 30 min.

The resultant liquid mixture was transferred to a sealed high-pressure crystallizing kettle, and dynamic crystallization was carried out at 200° C. for 48 h.

Figure 8:
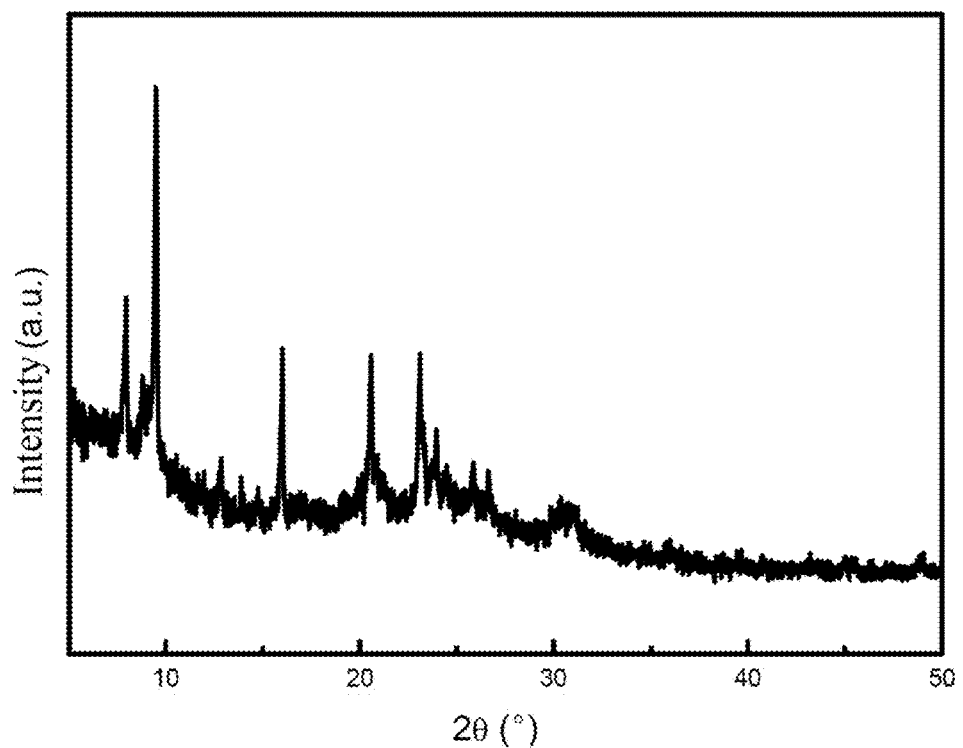
FIG. 8 is an XRD pattern of the composite material obtained in Example 7.

The product was taken out and allowed to stand and precipitate for 5 min. The non-in situ products in the upper layer of liquid were removed, and the precipitated in situ product was separated by centrifuging, washed, dried at 120° C. for 6 h, subjected to ammonium exchange treatment twice in 0.5 M ammonium chloride (in each exchange, the in situ product was put in an aqueous solution of ammonium chloride and stirred at 80° C. for 3 h), and baked at 550° C. for 4 h, to obtain a composite molecular sieve of SAPO-34/ZSM-5@kaolin microspheres. This product has an XRD pattern similar to that of the product prepared in Example 2. The content of SAPO-34 molecular sieve in the product was 12% by weight, and the content of ZSM-5 molecular sieve in the product was 6.8% by weight. The XRD pattern of the composite material is shown in FIG. 8.

Comparative Example 1

100 g kaolin, 350 g water, and 40 g alumina sol were homogeneously mixed and spray-dried to obtain kaolin microspheres, which were baked at 800° C. for 4 h and ready for use.

5 g phosphoric acid was weighed out and mixed with 15 g water. The mixture was stirred for 30 min, and 15 g water and 5 g triethylamine were added thereto under stirring, following by further stirring. 5 g kaolin microspheres were added, and the mixture was allowed to stand for 2 h. The resultant gel comprised the following components in a molar ratio of $5R:0.20SiO_2:1.47Al_2O_3:2.6P_2O_5:166H_2O$.

The liquid mixture obtained in step (1) was transferred to a sealed high-pressure crystallizing kettle, and crystallization was carried out in a rotary oven at 200° C. for 48 h.

Figure 9:
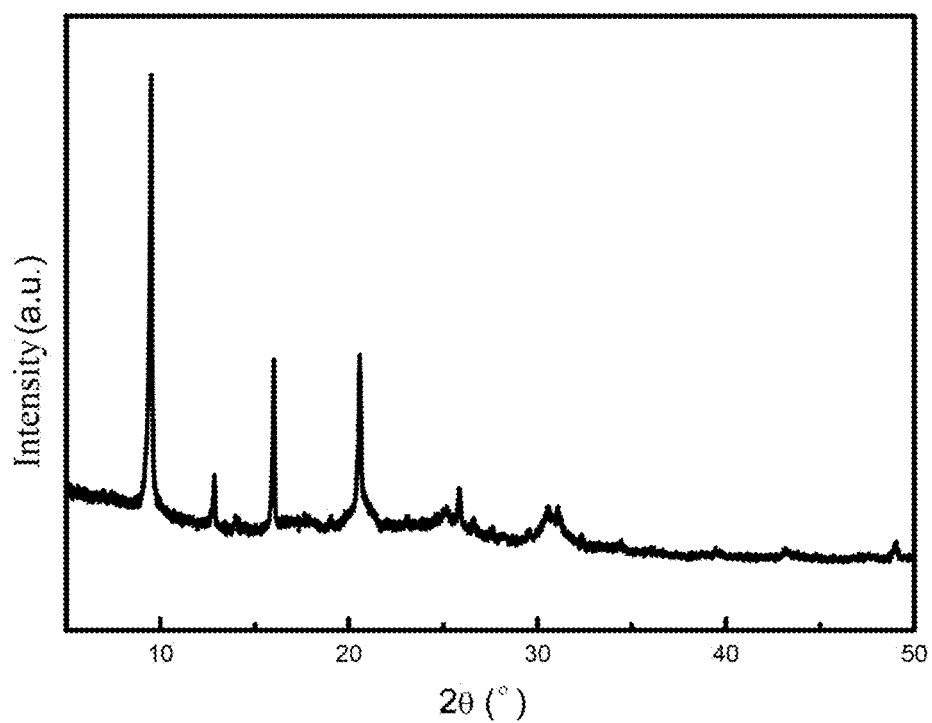
FIG. 9 is an XRD pattern of the composite material obtained in Comparative Example 1.
Figure 10A:
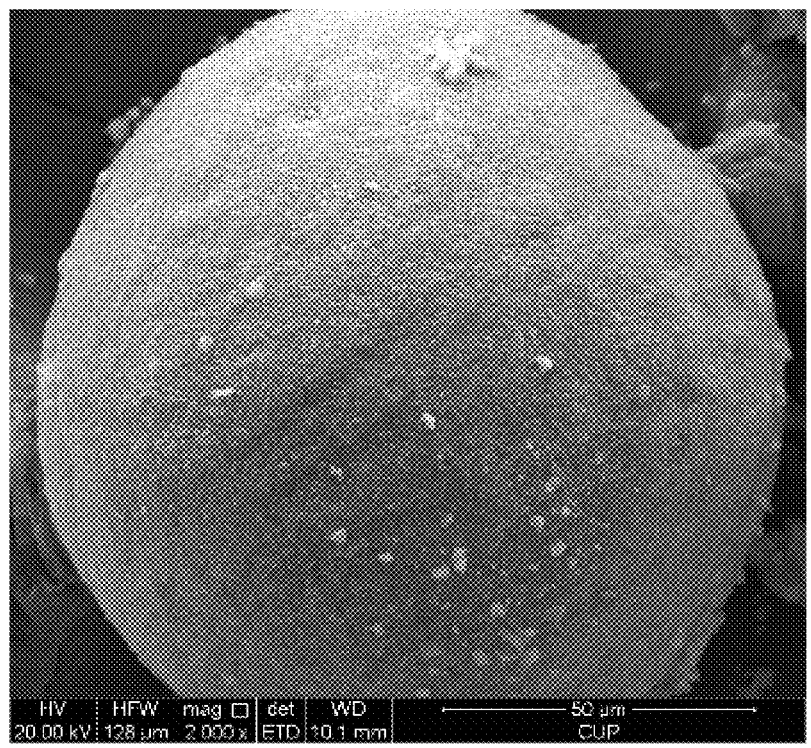
FIG. 10A is a 2000× magnification of an FESEM image of the composite material obtained in Comparative Example 1.
Figure 10B:
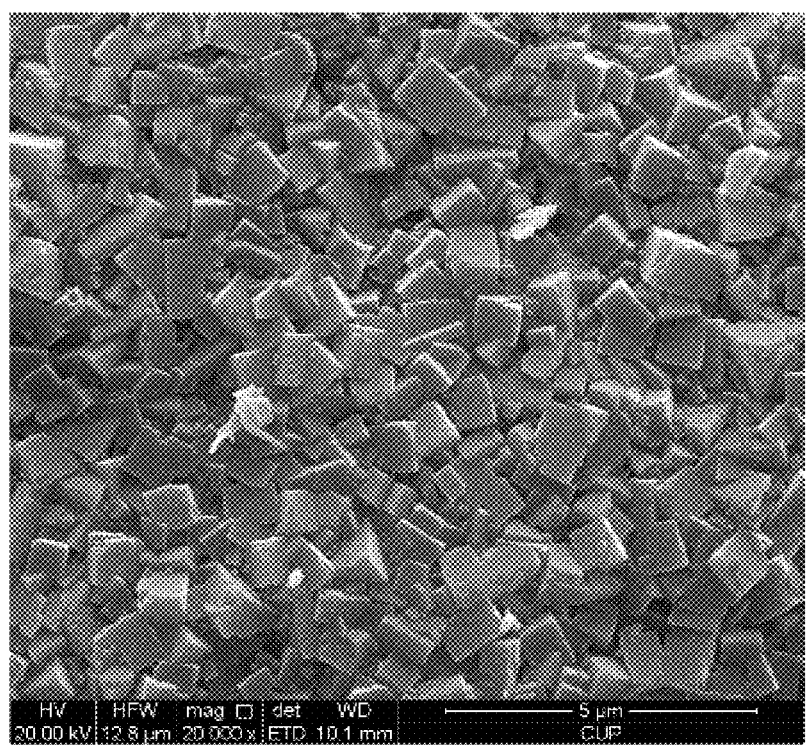
FIG. 10B is a 20000× magnification of a FESEM image of the composite material obtained in Comparative Example 1.

The product was taken out and allowed to stand and precipitate for 5 min. The non-in situ products in the upper layer of liquid were removed, and the precipitated in situ product was separated by centrifuging, washed, dried at 120° C. for 12 h, and baked at 550° C. for 4 h, to obtain a composite molecular sieve of SAPO-34@kaolin. After quantification by XRD, the content of SAPO-34 molecular sieve in the product was 30% by weight. The XRD pattern of the composite material is shown in FIG. 9, and the SEM images thereof are shown in FIG. 10.

Comparative Example 2

100 g kaolin, 350 g water, and 40 g alumina sol were homogeneously mixed and spray-dried to obtain kaolin microspheres, which were baked at 800° C. for 4 h and ready for use.

1.74 tetrapropylammonium bromide was weighed out and mixed with 70 g water. The mixture was stirred for 30 min. 5 g kaolin microspheres and 15 g water glass were added, and the mixture was stirred homogeneously.

The liquid mixture obtained above was transferred to a sealed high-pressure crystallizing kettle, and crystallization was carried out in a rotary oven at 170° C. for 48 h.

Figure 11:
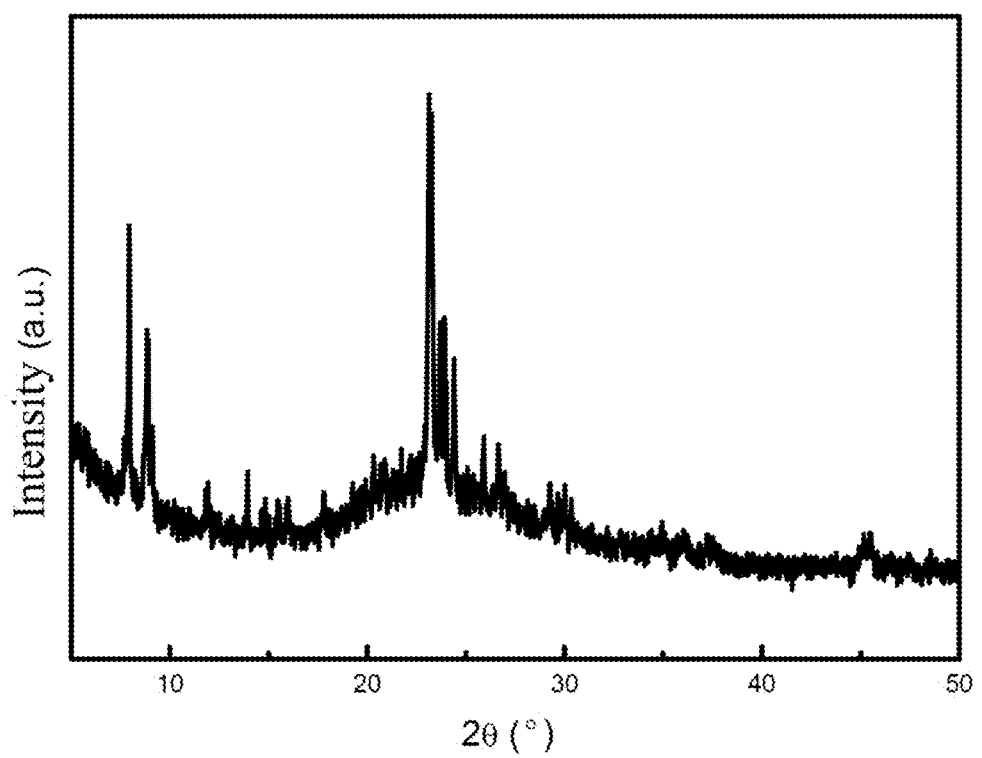
FIG. 11 is an XRD pattern of the composite material obtained in Comparative Example 2.
Figure 12A:
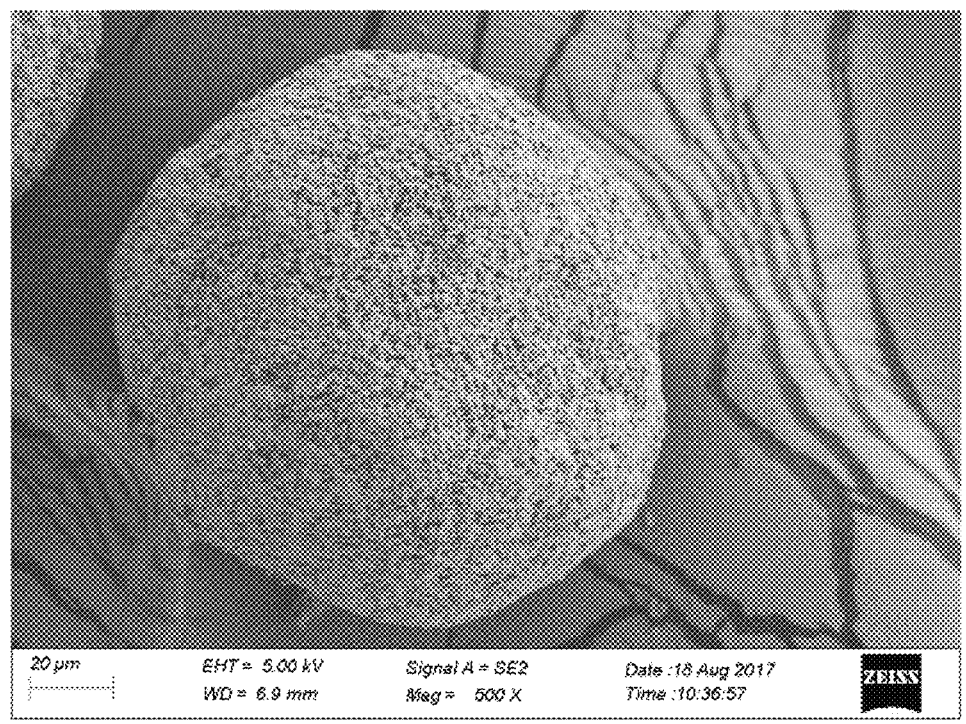
FIG. 12A is a 500× magnification of an FESEM image of the composite material obtained in Comparative Example 2.
Figure 12B:
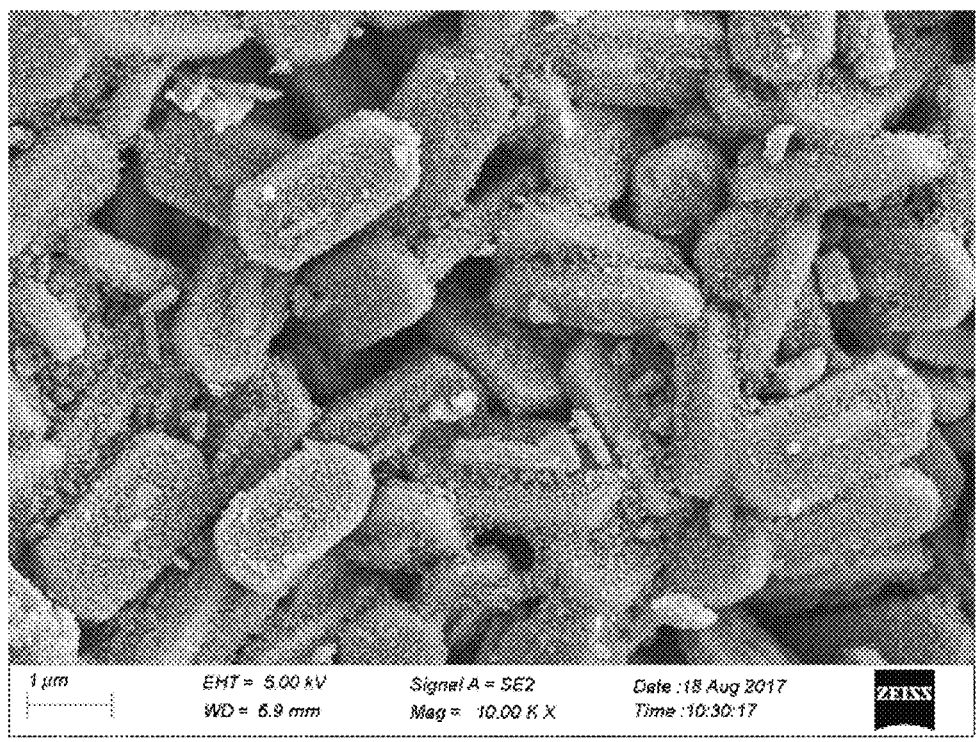
FIG. 12B is a 10000× magnification of a FESEM image of the composite material obtained in Comparative Example 2.

The product was taken out and allowed to stand and precipitate for 5 min. The non-in situ products in the upper layer of liquid were removed, and the precipitated in situ product was separated by centrifuging, washed, dried at 120° C. for 12 h, subjected to ammonium exchange treatment twice in 0.5 M ammonium chloride, and baked to obtain a composite molecular sieve of ZSM-5@kaolin. After quantification by XRD, the content of ZSM-5 molecular sieve in the product was 15% by weight. The XRD pattern of the composite material is shown in FIG. 11, and the SEM images thereof are shown in FIG. 12.

Comparative Example 3

The composite molecular sieve of SAPO-34@kaolin microspheres synthesized by the method of Comparative example 1 and the composite molecular sieve of ZSM-5@kaolin microspheres synthesized by the method of Comparative example 2 were physically mixed in a mass ratio of 1:1. The homogeneously mixed mixture was evaluated for catalytic activity.

Experimental Example 1: Catalytic Performance of the Composite Catalysts of SAPO-34/ZSM-5@Kaolin Microspheres With a small-scale fixed-bed catalytic reaction evaluating device, the catalytic performance of the composite catalytic materials of SAPO-34/ZSM-5@kaolin prepared in Examples 1-7, the SAPO-34@kaolin prepared in Comparative example 1, the ZSM-5@kaolin prepared in Comparative example 2, and the composite of SAPO-34@kaolin and ZSM-5@kaolin prepared in Comparative example 3 as a catalyst in an MTO reaction was evaluated.

For the evaluation, an aqueous solution of 95 wt % methanol was used as the starting material, and the conditions for evaluation were at a reaction temperature of 450° C., a weight hourly space velocity (WHSV) of 2.5 $h^{-1}$, and a carrier gas flow rate of 20 ml/min. The products after reaction were analyzed by off-line gas chromatography with a 3420A Gas Chromatographer (Beifen) using a HP PLOT-Q column and an FID detector for detection. When the methanol conversion was below 98 wt %, the catalyst was considered inactive, the experiment was stopped, and this time point was recorded as the catalyst life. The result of product selectivity was the maximum value among the samples taken during the methanol-to-olefin reaction. The results are shown in Table 1.

TABLE 1

Results of evaluation of catalytic performance in methanol-to-olefin (MTO) reaction

| Samples | Example 1 | Example 2 | Example 3 | Example 4 | Example 5 |
|---|---|---|---|---|---|
| Methanol conversion (wt. %) | 100 | 100 | 100 | 100 | 100 |
| Catalyst life (min) | 751 | 782 | 748 | 745 | 790 |
| Ethylene yield (wt. %) | 22 | 35 | 30 | 36 | 37 |
| Propylene yield (wt. %) | 46 | 40 | 42 | 37 | 40 |
| Yield of ethylene + propylene (wt. %) | 68 | 75 | 72 | 73 | 77 |
| Yield of ethylene + propylene + butylene (wt. %) | 83 | 89 | 84 | 85 | 86 |

| Samples | Example 6 | Example 7 | Comp. Ex. 1 | Comp. Ex. 2 | Comp. Ex. 3 |
|---|---|---|---|---|---|
| Methanol conversion (wt. %) | 100 | 100 | 100 | 100 | 100 |
| Catalyst life (min) | 775 | 740 | 51 | 1293 | 810 |
| Ethylene yield (wt. %) | 38 | 37 | 38 | 15 | 12 |
| Propylene yield (wt. %) | 40 | 42 | 40 | 38 | 43 |
| Yield of ethylene + propylene (wt. %) | 78 | 79 | 78 | 53 | 55 |
| Yield of ethylene + propylene + butylene (wt. %) | 89 | 89 | 91 | 71 | 73 |

The above experimental results demonstrate that by the method according to the present invention, the relative contents of SAPO-34 and ZSM-5 in the produced composite catalyst of SAPO-34/ZSM-5@kaolin microspheres can be changed by adjustment of the synthesis condition, and in turn the selectivity for ethylene and propylene in the MTO product can be adjusted. Meanwhile, as compared to the catalyst of SAPO-34@kaolin microspheres, the products synthesized in the examples have better activity and stability, and a catalyst life extended by 700 min or more; as compared to the catalyst of ZSM@kaolin and the mechanical catalyst of ZSM@kaolin+SAPO-35@kaolin, the products obtained according to the present invention result in better selectivity for ethylene, propylene, the duo (ethylene+propylene), and the trio (ethylene+propylene+butylene).

What is claimed is:

1. A method for preparing a composite catalytic material of SAPO-34/ZSM-5@kaolin microspheres, comprising the steps of:
   1) processing kaolin into kaolin microspheres, and baking the kaolin microspheres to obtain activated kaolin microspheres comprising $SiO_2$ and $Al_2O_3$;
   2) mixing the activated kaolin microspheres obtained in step 1), water, a phosphorus source ($P_2O_5$), and a template agent, in a molar ratio of (4-6)R:(0.20-0.30)$SiO_2$:(0.58-1.85)$Al_2O_3$:(2.0-3.1)$P_2O_5$:(111-222)$H_2O$, to prepare a gel;
   3) mixing the gel obtained in step 2) and a ZSM-5 molecular sieve, in a ZSM-5-to-gel mass ratio from 0.042 to 0.066, and carrying out aging, crystallization, and separation to obtain a composite material of SAPO-34/ZSM-5@kaolin;
   4) subjecting the composite material obtained in step 3) to ammonium exchange treatment, and baking, to obtain the composite catalytic material of SAPO-34/ZSM-5@kaolin microspheres.

2. The method according to claim 1, wherein step 1) comprises processing kaolin into kaolin microspheres by spray drying and baking the kaolin microspheres to obtain activated kaolin microspheres having a particle size of 80 to 100 μm.

3. The method according to claim 1, wherein step 2) comprises homogeneously mixing the phosphorus source with a part of water first, then adding the template agent and the rest of water, mixing them homogeneously, then adding the activated kaolin microspheres obtained in step 1), and mixing them homogeneously to obtain the gel.

4. The method according to claim 1, wherein the template agent is selected from one or more of triethylamine, diethylamine, and tetraethylammonium hydroxide.

5. The method according to claim 1, wherein the phosphorus source is phosphoric acid.

6. The method according to claim 1, wherein step 3) comprises mixing the gel obtained in step 2) and the ZSM-5 molecular sieve wherein the ZSM-5 has a Si/Al molar ratio from 50 to 200; carrying out aging at an aging temperature of 40° C. to 90° C. and crystallization at a crystallization temperature of 180° C. to 220° C.; and wherein the separation to obtain the composite material of SAPO-34/ZSM-5@kaolin comprises the steps of precipitation, centrifuging, washing, and drying.

7. The method according to claim 6, wherein the ZSM-5 molecular sieve has a Si/Al molar ratio from 50 to 150.

8. The method according to claim 6, wherein the aging is carried out at an aging temperature of 40° C. to 90° C. for 15 to 60 min.

9. The method according to claim 6, wherein the crystallization is carried out at a crystallization temperature of 180° C. to 220° C. for 24 to 72 h.

10. The method according to claim 1, wherein in step 3), the separation comprises the steps of precipitation, centrifuging, washing, and drying.

11. The method according to claim 1, wherein step 4) comprises subjecting the composite material obtained in step 3) to ammonium exchange treatment in an aqueous solution of ammonium chloride, drying, and baking, to obtain the composite catalytic material of SAPO-34/ZSM-5@kaolin microspheres.

12. The method according to claim 11, wherein in step 4), the aqueous solution of ammonium chloride has a molar concentration of 0.1 to 1 M.

13. The method according to claim 11, wherein in step 4), the ammonium exchange treatment comprises stirring the composite material obtained in step 3) in an aqueous solution of ammonium chloride for 2 to 6 h at 60° C. to 90° C.

14. The method according to claim 1, wherein in Step 4), the baking temperature is 500° C. to 600° C., and the baking duration is 3 to 6 h.

15. The method according to claim 1, wherein step 1) comprises processing kaolin into kaolin microspheres by mixing kaolin with water and a binder and then spray-drying the mixture to prepare kaolin microspheres, the mass ratio of the kaolin to the binder is from 1.5 to 2.75.

16. The method according to claim 15, wherein the binder is selected from one or more of water glass, alumina sol, and silica sol.

17. The method according to claim 15, wherein step 1) comprises baking the kaolin microspheres to obtain activated kaolin microspheres at a baking temperature of 650° C. to 900° C. for a baking duration of 1 to 6 h.

18. A composite catalytic material of SAPO-34/ZSM-5 @kaolin microspheres prepared by the method according to claim 1, wherein, based on the relative crystallinity, the relative content of the SAPO-34 molecular sieve is 7 to 15 wt %, and the relative content of the ZSM-5 molecular sieve is 6 to 12 wt %.

19. A method for producing olefins from methanol, comprising:
    providing an aqueous solution of methanol as a raw material;
    contacting the composite catalytic material of SAPO-34/ZSM-5@kaolin microspheres according to claim 9 as a catalyst to prepare olefins from the raw material.

20. The method according to claim 19, wherein, the olefins are prepared at the conditions of normal pressure, a reaction temperature of 400° C. to 500° C., and a weight hourly space velocity (WHSV) of 2 to 3 $h^{-1}$.

* * * * *